(12) United States Patent
Gatzemeyer et al.

(10) Patent No.: US 8,225,449 B2
(45) Date of Patent: Jul. 24, 2012

(54) INTERACTIVE TOOTHBRUSH

(75) Inventors: John Gatzemeyer, Hillsborough, NJ (US); Eduardo Jimenez, Manalapan, NJ (US); Glen Biron, Cedar Park, TX (US); Mark Delz, Round Rock, TX (US); Tim Hopkins, Round Rock, TX (US); Russell Read, Round Rock, TX (US); Doulgas Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 892 days.

(21) Appl. No.: 12/137,933

(22) Filed: Jun. 12, 2008

(65) Prior Publication Data

US 2008/0307594 A1 Dec. 18, 2008

Related U.S. Application Data

(63) Continuation-in-part of application No. 11/677,433, filed on Feb. 21, 2007, now Pat. No. 7,845,041, which is a continuation-in-part of application No. 11/413,624, filed on Apr. 28, 2006, now Pat. No. 7,418,757.

(60) Provisional application No. 60/738,528, filed on Nov. 21, 2005, provisional application No. 60/677,192, filed on May 3, 2005.

(51) Int. Cl.
  *A46B 15/00* (2006.01)
(52) U.S. Cl. .......................................... 15/105; 15/167.1
(58) Field of Classification Search .................... 15/105, 15/167.1, 22.1
See application file for complete search history.

(56) References Cited

U.S. PATENT DOCUMENTS

| | | | |
|---|---|---|---|
| 1,986,955 | A | 1/1935 | Bedell |
| 2,877,477 | A | 3/1959 | Levin |
| 2,947,013 | A | 8/1960 | Silverman |
| 3,027,507 | A | 3/1962 | Hübner |
| D210,349 | S | 3/1968 | Boldt |
| 3,458,794 | A | 7/1969 | Bohnstedt |

(Continued)

FOREIGN PATENT DOCUMENTS

CA 2267732 10/2000

(Continued)

OTHER PUBLICATIONS

"iBrush—the toothbrush that makes you never want to stop brushing your teeth". http://www.cs.chalmers.se.idc/ituniv/student/2003/ubicomp/ibrush.htm. Published 2003. Retrieved May 19, 2006.

(Continued)

*Primary Examiner* — Shay Karls
(74) *Attorney, Agent, or Firm* — Amy M. Fernandez

(57) ABSTRACT

A toothbrush (100) may include an audio component (140) configured to operate as a microphone to receive an audio signal in a first mode of operation and to operate as a speaker to output the audio signal through the body (148) of the toothbrush (100) in a second mode of operation. Another toothbrush (100) may include a motor (271) for powering one or more moveable elements (227) and a processor (392) to monitor and maintain a variable, such as the motor speed or voltage applied, associated with the motor (271). Another toothbrush (100) may include a single operation mode button (FIGS. 13A-13C) to change a mode of operation of moveable elements (227) on the toothbrush (100) and audio signals transmitted through an output (148) of the toothbrush (100).

11 Claims, 11 Drawing Sheets

U.S. PATENT DOCUMENTS

| | | |
|---|---|---|
| 4,075,458 A | 2/1978 | Moyer |
| 4,341,230 A | 7/1982 | Siahou |
| 4,479,516 A | 10/1984 | Hunter |
| 4,603,448 A | 8/1986 | Middleton et al. |
| 4,698,869 A | 10/1987 | Mierau et al. |
| 4,716,614 A | 1/1988 | Jones et al. |
| 4,744,124 A | 5/1988 | Wang |
| 4,764,961 A | 8/1988 | Hung |
| 4,766,630 A | 8/1988 | Hegemann |
| 4,788,734 A | 12/1988 | Bauer |
| 4,845,796 A | 7/1989 | Mosley |
| 4,866,807 A | 9/1989 | Kreit |
| D304,779 S | 11/1989 | Raphael et al. |
| D304,780 S | 11/1989 | Morris, Jr. |
| D304,781 S | 11/1989 | Hanson |
| 4,944,016 A | 7/1990 | Christian |
| 4,944,704 A | 7/1990 | Grace |
| 5,006,779 A | 4/1991 | Fenne |
| 5,044,037 A | 9/1991 | Brown |
| D321,986 S | 12/1991 | Snyder et al. |
| 5,115,533 A | 5/1992 | Hukuba |
| 5,133,102 A | 7/1992 | Sakuma |
| 5,165,131 A | 11/1992 | Staar |
| D340,455 S | 10/1993 | Christian |
| 5,259,086 A | 11/1993 | Fong |
| 5,314,336 A | 5/1994 | Diamond et al. |
| 5,335,798 A | 8/1994 | Bonwell |
| 5,337,435 A | 8/1994 | Krasner |
| 5,339,479 A | 8/1994 | Lyman |
| 5,341,534 A | 8/1994 | Serbinski et al. |
| D353,490 S | 12/1994 | Hartwein |
| D354,168 S | 1/1995 | Hartwein |
| 5,438,726 A | 8/1995 | Leite |
| D363,605 S | 10/1995 | Kou et al. |
| 5,493,747 A | 2/1996 | Inakagata et al. |
| 5,504,961 A | 4/1996 | Yang |
| D371,242 S | 7/1996 | Shimatsu et al. |
| D373,023 S | 8/1996 | Otero et al. |
| 5,544,382 A | 8/1996 | Giuliani et al. |
| D375,841 S | 11/1996 | Serbinski |
| 5,572,762 A | 11/1996 | Scheiner |
| 5,628,641 A | 5/1997 | Hahn |
| 5,673,451 A | 10/1997 | Moore et al. |
| 5,675,859 A | 10/1997 | Barre |
| 5,697,117 A | 12/1997 | Craft |
| D388,958 S | 1/1998 | Hartwein |
| 5,704,087 A | 1/1998 | Strub |
| 5,784,742 A | 7/1998 | Giuliani et al. |
| 5,786,749 A | 7/1998 | Johnson |
| D397,252 S | 8/1998 | Allende |
| 5,810,601 A | 9/1998 | Williams |
| D403,511 S | 1/1999 | Serbinski |
| 5,864,288 A | 1/1999 | Hogan |
| 5,894,453 A | 4/1999 | Pond |
| 5,901,397 A | 5/1999 | Hafele et al. |
| 5,924,159 A | 7/1999 | Haitin |
| 5,960,507 A | 10/1999 | Dutra et al. |
| 5,974,616 A | 11/1999 | Dreyfus |
| 5,994,855 A | 11/1999 | Lundell et al. |
| 6,029,303 A | 2/2000 | Dewan |
| D426,708 S | 6/2000 | Francis |
| 6,081,957 A | 7/2000 | Webb |
| 6,115,477 A | 9/2000 | Filo |
| 6,154,912 A | 12/2000 | Li |
| D436,254 S | 1/2001 | Kling et al. |
| 6,199,239 B1 | 3/2001 | Dickerson |
| 6,202,242 B1 | 3/2001 | Salmon et al. |
| 6,202,245 B1 | 3/2001 | Khodadadi |
| D440,766 S | 4/2001 | Hartwein et al. |
| 6,237,178 B1 | 5/2001 | Krammer et al. |
| 6,325,066 B1 | 12/2001 | Hughes |
| D453,996 S | 3/2002 | Kling et al. |
| D455,556 S | 4/2002 | Kling |
| 6,389,633 B1 | 5/2002 | Rosen |
| D458,028 S | 6/2002 | McCurrach |
| 6,397,424 B1 | 6/2002 | Leung |
| 6,421,866 B1 | 7/2002 | McDougall |
| D467,432 S | 12/2002 | Callendrille, Jr. |
| 6,536,068 B1 | 3/2003 | Yang |
| 6,554,619 B2 | 4/2003 | Williams |
| D474,895 S | 5/2003 | Breit |
| D475,529 S | 6/2003 | Wright et al. |
| 6,581,233 B1 | 6/2003 | Cheng |
| D476,485 S | 7/2003 | Mulder et al. |
| D478,423 S | 8/2003 | Mulder et al. |
| 6,606,755 B1 | 8/2003 | Robinson et al. |
| 6,611,780 B2 | 8/2003 | Lundell |
| 6,619,969 B2 | 9/2003 | Scheider |
| D480,563 S | 10/2003 | Hensel |
| 6,633,747 B1 | 10/2003 | Reiss |
| 6,648,641 B1 | 11/2003 | Viltro |
| D484,312 S | 12/2003 | Li |
| 6,658,687 B1 | 12/2003 | McDonald |
| D489,183 S | 5/2004 | Akahori et al. |
| D489,534 S | 5/2004 | Hensel |
| 6,731,213 B1 | 5/2004 | Smith |
| D492,118 S | 6/2004 | McCurrach et al. |
| D493,960 S | 8/2004 | Jimenez et al. |
| 6,779,216 B2 | 8/2004 | Davies et al. |
| D496,653 S | 9/2004 | Townsend et al. |
| 6,792,640 B2 | 9/2004 | Lev |
| 6,795,993 B2 | 9/2004 | Lin |
| 6,799,346 B2 | 10/2004 | Jeng et al. |
| 6,826,350 B1 | 11/2004 | Kashino et al. |
| D500,207 S | 12/2004 | Jimenez et al. |
| D500,208 S | 12/2004 | Vu |
| D500,209 S | 12/2004 | Kellogg |
| 6,836,918 B1 | 1/2005 | Wong |
| 6,845,537 B2 | 1/2005 | Wong |
| D502,601 S | 3/2005 | Lamason et al. |
| D503,537 S | 4/2005 | Lamason et al. |
| D503,852 S | 4/2005 | Hensel |
| 6,883,199 B1 | 4/2005 | Lundell et al. |
| 6,920,660 B2 | 7/2005 | Lam |
| 6,923,409 B2 | 8/2005 | Strunk |
| D510,930 S | 10/2005 | Deguchi |
| 6,952,855 B2 | 10/2005 | Lev et al. |
| 6,954,961 B2 | 10/2005 | Ferber et al. |
| D511,519 S | 11/2005 | Bone et al. |
| D515,815 S | 2/2006 | Jimenez et al. |
| D515,816 S | 2/2006 | Jimenez et al. |
| 7,003,839 B2 | 2/2006 | Hafliger et al. |
| 7,013,522 B2 | 3/2006 | Kumagai |
| 7,049,790 B2 | 5/2006 | Pfenniger et al. |
| 7,055,531 B2 | 6/2006 | Rehkemper |
| 7,086,111 B2 | 8/2006 | Hilscher et al. |
| D529,044 S | 9/2006 | Andre et al. |
| D531,190 S | 10/2006 | Lee et al. |
| 7,120,960 B2 | 10/2006 | Hilscher et al. |
| D533,349 S | 12/2006 | Jimenez et al. |
| D533,720 S | 12/2006 | Vu |
| D534,726 S | 1/2007 | Vu |
| D534,728 S | 1/2007 | Vu |
| D534,921 S | 1/2007 | Andre et al. |
| D535,308 S | 1/2007 | Andre et al. |
| D538,267 S | 3/2007 | Christianson et al. |
| D538,297 S | 3/2007 | Ching |
| D539,813 S | 4/2007 | Chen |
| D539,817 S | 4/2007 | Reverberi |
| 7,418,757 B2 | 9/2008 | Gatzerneyer et al. |
| 2001/0004428 A1 | 6/2001 | Horng |
| 2002/0067084 A1 | 6/2002 | Jung |
| 2002/0092104 A1* | 7/2002 | Ferber et al. .................. 15/22.1 |
| 2002/0174498 A1 | 11/2002 | Li |
| 2003/0017874 A1 | 1/2003 | Jianfei |
| 2003/0221269 A1 | 12/2003 | Zhuan |
| 2003/0232303 A1 | 12/2003 | Black |
| 2004/0000017 A1 | 1/2004 | Kumagai |
| 2004/0074026 A1 | 4/2004 | Blaustein et al. |
| 2004/0123409 A1 | 7/2004 | Dickie |
| 2004/0134000 A1 | 7/2004 | Hilfinger et al. |
| 2004/0163191 A1 | 8/2004 | Cuffaro et al. |
| 2004/0255409 A1 | 12/2004 | Hilscher |
| 2005/0000537 A1 | 1/2005 | Junkins |
| 2005/0011022 A1 | 1/2005 | Kwong |
| 2005/0022322 A1 | 2/2005 | Jimenez et al. |
| 2005/0066461 A1 | 3/2005 | Chang |

| | | | |
|---|---|---|---|
| 2005/0144744 A1 | 7/2005 | Thiess et al. | |
| 2005/0150067 A1 | 7/2005 | Cobabe et al. | |
| 2005/0152231 A1 | 7/2005 | Yeh | |
| 2005/0172433 A1 | 8/2005 | Oliver | |
| 2005/0204490 A1 | 9/2005 | Kemp et al. | |
| 2005/0278882 A1* | 12/2005 | Drzewiecki et al. | 15/105 |
| 2005/0283929 A1 | 12/2005 | Jimenez et al. | |
| 2006/0037158 A1 | 2/2006 | Foley et al. | |
| 2006/0048315 A1 | 3/2006 | Chan et al. | |
| 2006/0057513 A1 | 3/2006 | Ito et al. | |
| 2006/0104456 A1 | 5/2006 | Filo et al. | |
| 2006/0123570 A1 | 6/2006 | Pace et al. | |
| 2006/0130253 A1 | 6/2006 | Rycroft | |
| 2006/0150350 A1 | 7/2006 | Pfenniger et al. | |
| 2006/0179591 A1 | 8/2006 | Spooner | |
| 2007/0039109 A1 | 2/2007 | Nanda | |
| 2007/0074359 A1 | 4/2007 | O'Lynn | |
| 2007/0094822 A1* | 5/2007 | Gatzemeyer et al. | 15/105 |
| 2007/0190509 A1* | 8/2007 | Kim | 434/263 |
| 2007/0192976 A1 | 8/2007 | Gatzemeyer et al. | |
| 2007/0261185 A1 | 11/2007 | Guney et al. | |
| 2008/0028553 A1* | 2/2008 | Batthauer | 15/105 |

FOREIGN PATENT DOCUMENTS

| | | |
|---|---|---|
| CA | 2409908 | 11/2002 |
| CA | ID98346 | 1/2004 |
| CA | ID102709 | 1/2004 |
| CA | 2499371 | 4/2004 |
| CA | 2530337 | 1/2005 |
| CA | 2545676 | 5/2005 |
| CA | 2553568 | 9/2005 |
| CA | 2508994 | 12/2005 |
| CA | 2559039 | 6/2006 |
| CA | 2589817 | 6/2006 |
| CA | 2591798 | 7/2006 |
| CN | 2461373 Y | 11/2001 |
| CN | 2537277 Y | 2/2003 |
| CN | 1470205 | 1/2004 |
| CN | 2614048 Y | 5/2004 |
| CN | 3367849D | 5/2004 |
| CN | 1556994 | 12/2004 |
| CN | 3666650D | 7/2007 |
| CN | 2933335 Y | 8/2007 |
| DE | 31 49 233 | 4/1983 |
| DE | 19811676 | 9/1999 |
| DE | 29915858 | 1/2000 |
| DE | 10254613 | 6/2004 |
| EP | 0 435 329 | 7/1991 |
| EP | 0435329 | 7/1991 |
| EP | 0634151 | 1/1995 |
| EP | 1609389 | 12/2005 |
| EP | 1698252 | 9/2006 |
| JP | 01008914 | 1/1989 |
| JP | 2003/180717 | 7/2003 |
| JP | 2003180717 | 7/2003 |
| JP | 2004/065838 | 3/2004 |
| JP | 2004065838 | 3/2004 |
| JP | 2004/105246 | 4/2004 |
| JP | 2004105246 | 4/2004 |
| KR | 2007107197 A * | 11/2007 |
| RU | 2013968 | 6/1994 |
| RU | 2216295 | 11/2003 |
| WO | WO 97/00650 | 1/1997 |
| WO | WO 98/55274 | 12/1998 |
| WO | WO 99/32011 | 7/1999 |
| WO | WO 00/74591 | 12/2000 |
| WO | WO 03/085670 | 10/2003 |
| WO | WO 2004/026077 | 4/2004 |
| WO | WO 2004/098445 | 11/2004 |
| WO | WO 2005/000150 | 1/2005 |
| WO | WO 2005/074745 | 8/2005 |
| WO | WO 2006/002101 | 1/2006 |
| WO | WO 2006/057513 | 6/2006 |
| WO | WO 2006/065159 | 6/2006 |
| WO | WO 2006/119205 | 11/2006 |
| WO | WO 2006/137648 | 12/2006 |
| WO | WO 2007/032015 | 3/2007 |
| WO | WO 2007/068984 | 6/2007 |
| WO | WO 2007/089638 | 8/2007 |
| WO | WO 2007/097886 | 8/2007 |
| WO | WO 2007/106757 | 9/2007 |

OTHER PUBLICATIONS

Translation of Office Action issued by the Taiwan Intellectual Property Office, dated Mar. 31, 2011, for Taiwan Patent Application No. 097105828.

Partial International Search Report in International Application No. PCT/US08/068298, mailed Feb. 18, 2009.

International Search Report and Written Opinion in International Application No. PCT/US08/068298, mailed Jun. 10, 2009.

International Search Report in International Application No. PCT/US08/053920, mailed Sep. 29, 2008.

* cited by examiner

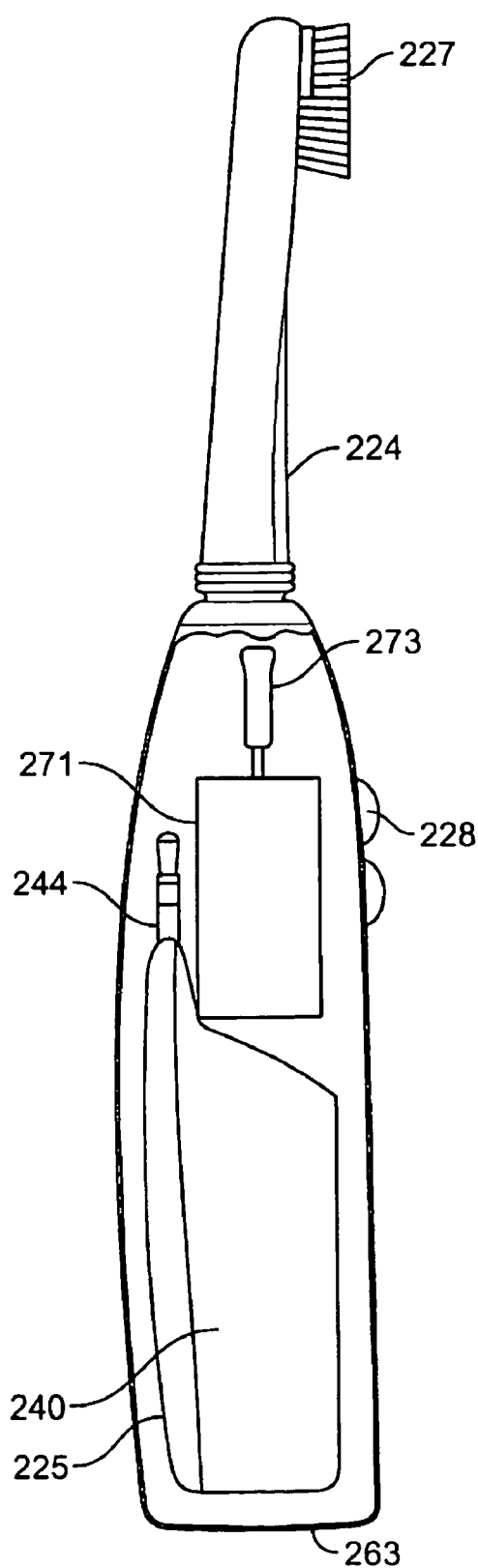
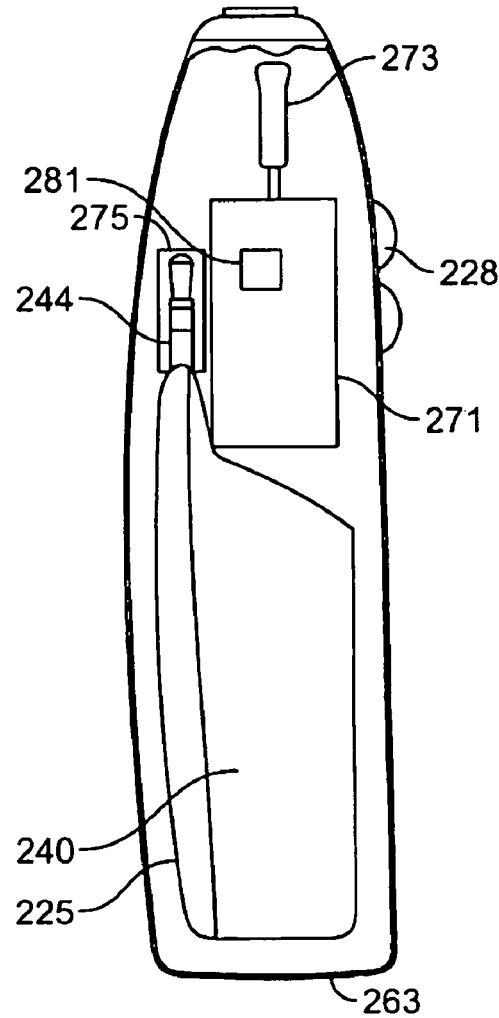
FIG. 6
FIG. 7

INTERACTIVE TOOTHBRUSH

CROSS-REFERENCE TO RELATED APPLICATIONS

This application is a continuation-in-part of U.S. patent application Ser. No. 11/677,433 filed, Feb. 21, 2007, which is a continuation-in-part of U.S. patent application Ser. No. 11/413,624 filed, Apr. 28, 2006, which claims the benefit of priority of U.S. Provisional Application 60/738,528, filed Nov. 21, 2005, and U.S. Provisional Application 60/677,192, filed May 3, 2005, all of which are incorporated by reference herein in their entirety.

BACKGROUND OF THE INVENTION

Aspects of the present disclosure relate to toothbrushes, and more particularly to a toothbrush that can record and/or play music or other audio signals. Statistics show that only a small percentage of the population in any country brushes their teeth for the dentist-recommended time of two minutes. This can be especially true of younger children and teenagers, who view tooth brushing as a mundane duty with few pleasurable aspects. Accordingly, there is a need to create an environment that makes tooth brushing enjoyable so that children and teenagers in particular will brush as often as they should and for the recommended period of time.

BRIEF SUMMARY OF THE INVENTION

Aspects of the present disclosure enable a person to know that he/she has brushed his/her teeth for a period of time close to the professional recommendation while enjoying a musical interlude of his/her choosing.

In one aspect, a toothbrush is provided with a body configured to store a speaker that is configured to output an audio signal through the body of the toothbrush and configured to be angled with respect to the body to prevent water from contacting the speaker.

In another aspect, a toothbrush comprises a body configured to store an audio component that is configured to operate as a microphone to receive an audio signal in a first mode of operation and to operate as a speaker to output the audio signal through the body of the toothbrush in a second mode of operation.

In another aspect, a toothbrush comprises a motor for operation of one or more moveable elements of the toothbrush and a processor configured to automatically monitor and maintain a variable associated with the motor during operation of the motor.

In another aspect, a toothbrush comprises a body, a portion of the body being configured for gripping by a user; a storage unit including an output for transmitting a stored audio signal and a power source, wherein the storage unit is configured to be removably housed within a cavity of the body; an oral care region attached to the body, the oral care region including tooth cleaning elements configured to move when powered by the power source; and a single operation mode button configured to change a mode of operation of the toothbrush.

A variety of different storage unit and toothbrush configurations are discussed herein, each creating an enjoyable environment during tooth brushing. These configurations advantageously provide improved oral hygiene for children and teenagers.

BRIEF DESCRIPTION OF THE DRAWINGS

FIG. 6 is a cutaway side view illustrating internal components of the toothbrush of FIG. 5 described herein.

FIG. 7 is an enlarged internal view of a toothbrush described herein.

DETAILED DESCRIPTION OF THE INVENTION

Figure 1:
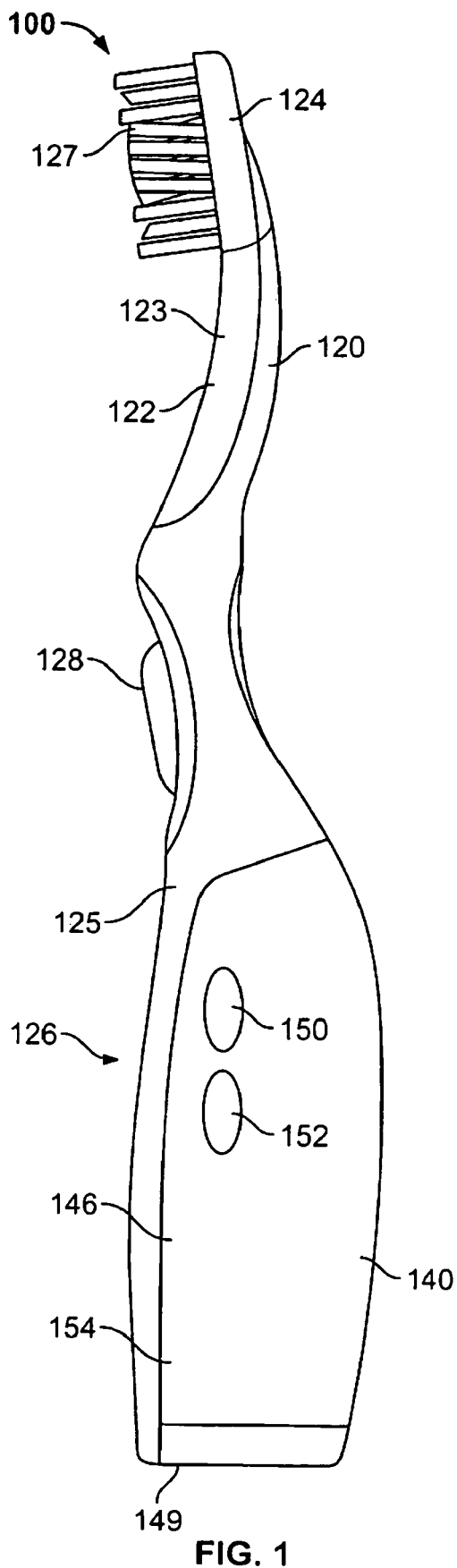
FIG. 1 is a side view of an example of a toothbrush described herein.

The following detailed description is not intended to be understood in a limiting sense, but to be examples of the disclosure presented solely for illustration thereof, and by reference to which in connection with the following description and the accompanying drawings one skilled in the art may be advised of the advantages and construction of the disclosure. In the various views of the drawings, like reference characters designate like or similar parts.

FIGS. 1-4 illustrate a toothbrush assembly 100 in accordance with at least one aspect of the present disclosure. The toothbrush assembly 100 may include a power toothbrush 120 having a body 125, a removable storage unit 140 that forms a portion of the handle 126, and an operation mode button 128. The toothbrush 120 further may comprise a head 124 or oral care region having tooth cleaning elements 127, and a handle 126. Head 124 may be replaceable, or it may be permanently attached to handle 126. As used herein, the term "tooth cleaning elements" or "cleaning elements" may includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements may include but are not limited to tufts of bristles that can be formed to have a number of different shapes and sizes and elastomeric cleaning members that can be formed to have a number of different shapes and sizes, or a combination of both tufts of bristles and elastomeric cleaning members. The tooth cleaning elements may be arranged on head 124 as desired.

The toothbrush 120 may be a powered toothbrush including a power source that drives a powered element, such as movable cleaning elements 127.

Figure 2:
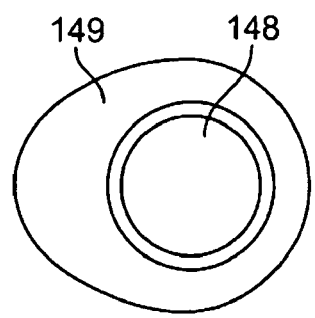
FIG. 2 is a bottom view of the surface of the toothbrush of FIG. 1 in accordance with at least one aspect of the present disclosure.
Figure 3:
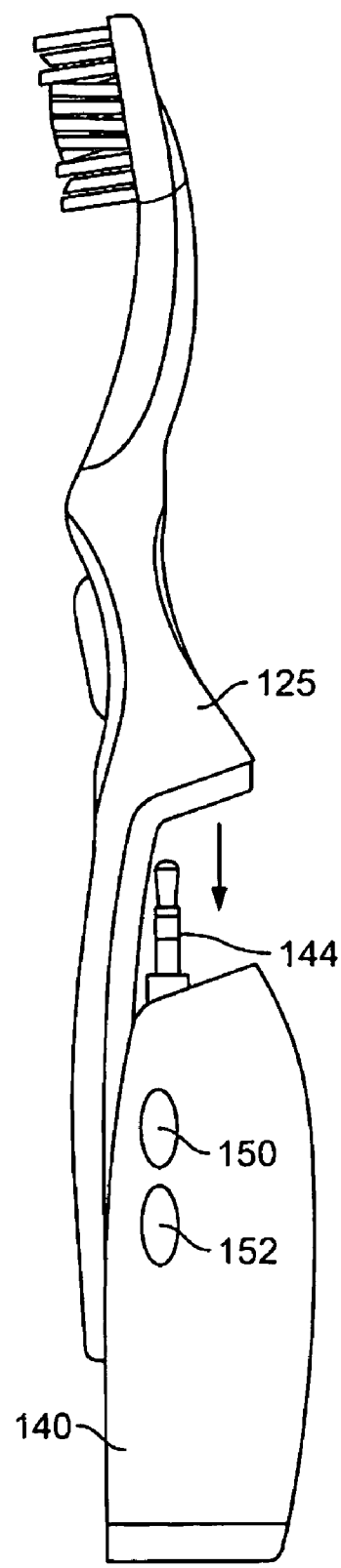
FIG. 3 is an exploded view of the toothbrush of FIG. 1 described herein.
Figure 4:
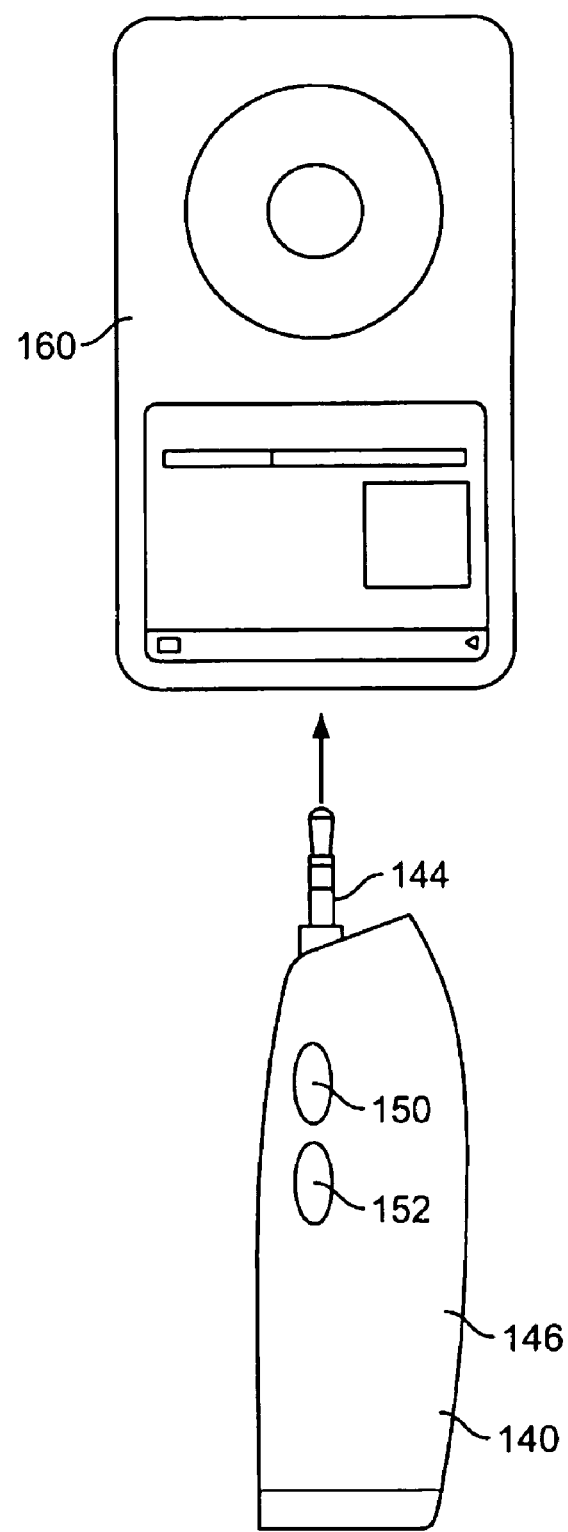
FIG. 4 is an exploded view of a connection arrangement of a storage unit of the toothbrush of FIG. 1 and a signal source described herein.

Referring to FIGS. 1-4, the removable storage unit 140 further may comprise an input 144 for connection to an audio device 160, a digital memory device 146 (shown in dotted lines) for storing audio signals in digital form in which signal are received via the input 144. The input can take on a variety of forms. For example, in one arrangement, input 144 may be a standard headphone jack (i.e. 2.5 mm). Referring to FIG. 2, the removable storage unit 140 may include an output 148 in the form of a speaker positioned on the underside 149 of the unit 140 for audibly transmitting the digitally stored audio signals to the user's surroundings. The speaker may be of sealed construction for water resistance, for example. The speaker 148 may be configured to be angled to prevent moisture/water collection from pooling on the surface in order to prevent water from contacting the speaker.

Figure 15:
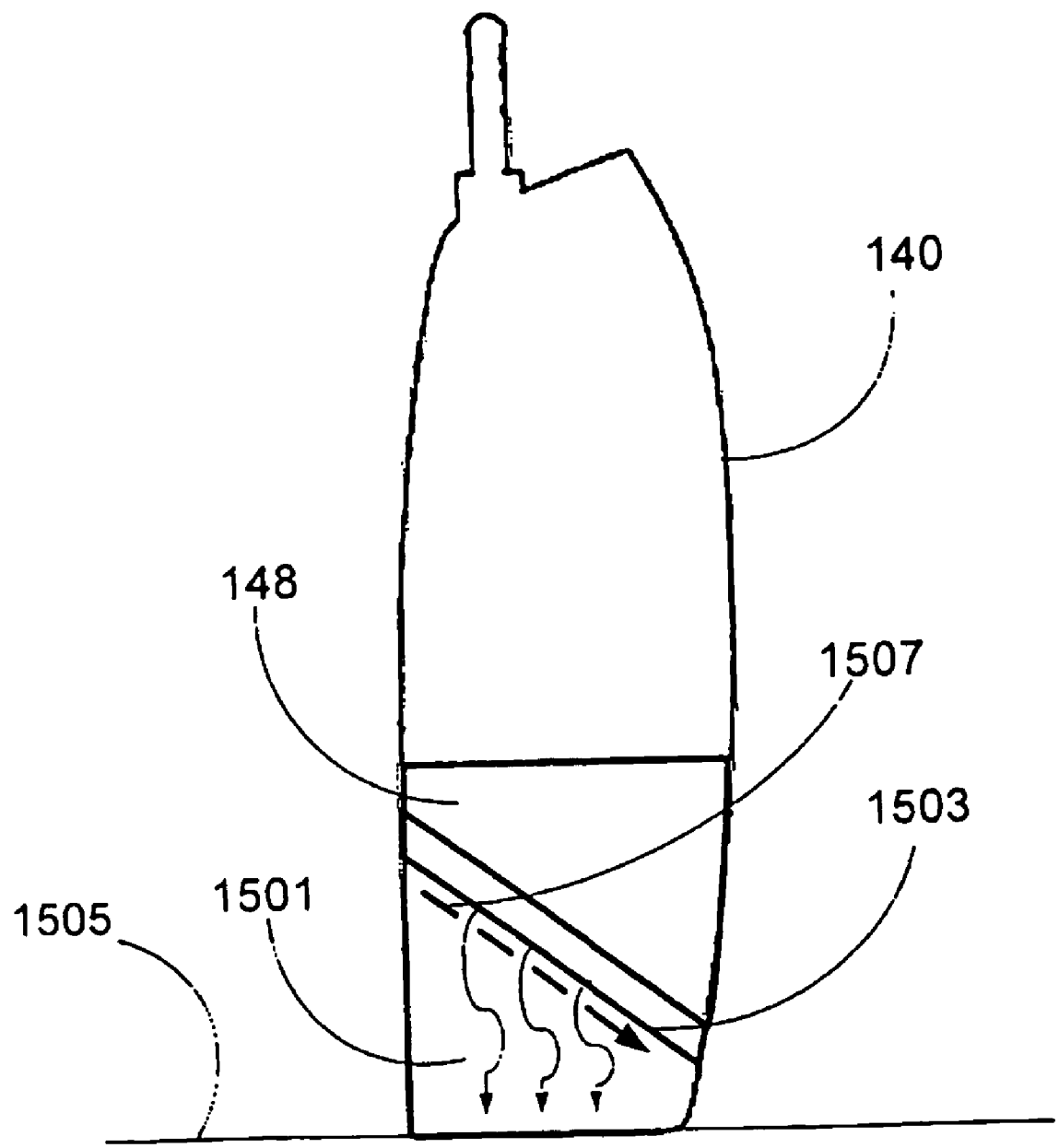
FIG. 15 is a cutaway side view of an example of a storage unit of a toothbrush described herein.

FIG. 15 is a cutaway side view of an example of a storage unit of toothbrush described herein. As shown in FIG. 15, storage unit 140 may include a speaker 148 that is configured to output audio 1501 through the base of the storage unit. The girth of the output opening 1503 of the speaker 148 may be configured to be angled with respect to a resting surface 1505 of the storage unit 140. As such, since the speaker opening 1503 is angled with respect to surface 1505, a larger speaker opening 1503 may be utilized to allow for a louder audio output 1501. The angle of the speaker opening 1503 with respect to surface 1505 may vary with respect to the girth of the speaker opening 1503 desired. In one embodiment, speaker opening 103 may be configured to be between 20 and 30 degrees, yet the present disclosure is not so limited.

Still further, by angling speaker opening 1503 with respect to surface 1505, if a user places the storage unit 140 on a surface 1505 that has a pool of water on the surface 1505, any possible moisture that may collect on the speaker opening 1503 surface may be drained, as shown by broken reference line 1507. As such, a user does not worry about cleaning a sink surface 1505 of all water before placing her toothbrush, with the storage unit 140 included, on the surface 1505.

Figure 14:
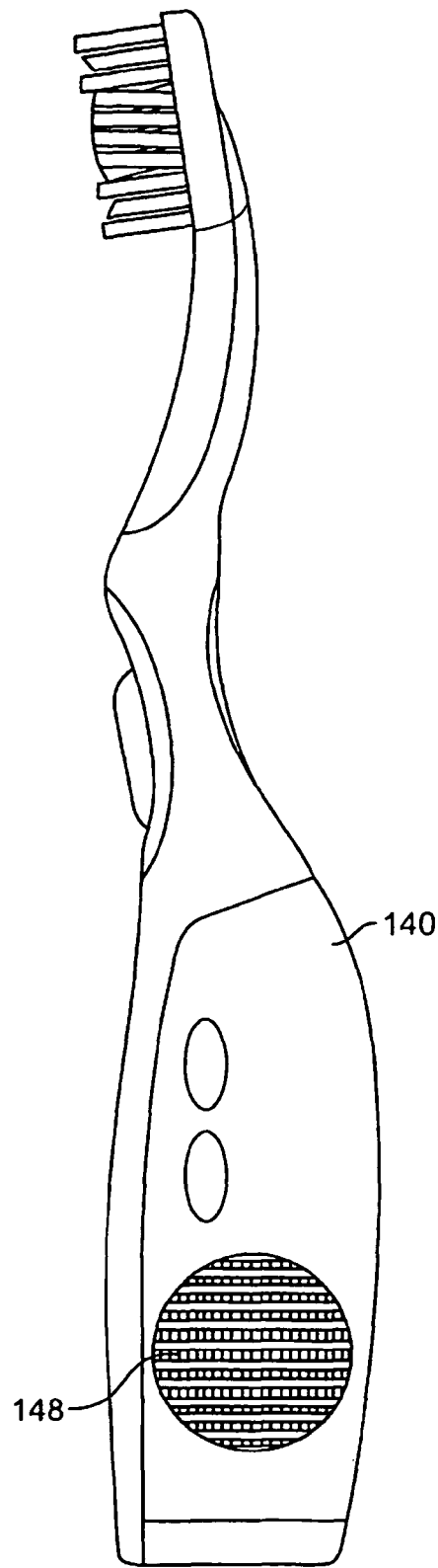
FIG. 14 is a side view of an example of a toothbrush described herein.

Additionally, the output 148 can be located at other parts of the storage unit 140. For example, as shown in FIG. 14, speaker 148 may be configured on a side of storage unit 140. In such a configuration, if the toothbrush 100 is standing so that underside 149 is against a surface, such as a bathroom counter, music or other audio output still may be heard without a muffled sound as the audio hits the surface beneath the underside 149. Still other configurations allow for multiple speakers 148 and/or speaker system that may include components to output sound in multiple directions.

Although not shown in the Figures, a microphone may be included within one or more of the components described herein. Such a microphone may be configured to allow a user to input audio speech or sounds as desired by the user. In accordance with at least one aspect of the present disclosure, speaker 148 may be an audio component configured to be utilized as both a speaker for output and a microphone for input. In accordance with one mode of operation, the audio component may operate as a microphone to receive an audio signal, such as speech or music. The received audio signal may be stored in a memory within the toothbrush. Then, in another mode of operation, the same audio component may be utilized as a speaker, such as speaker 148, to output an audio signal, such as the saved audio signal or another stored audio signal. The different modes of operation may be actuated by one or more operation mode buttons, such as operation mode button 128. Operation of the audio component as a microphone or as a speaker may be implemented by one or more different hardware, firmware, or software components to implement the desired mode of operation.

The storage unit 140 further may include a record button 150 for recording audio signals to the memory 146, and a play button 152 for playing the recorded audio signals. In operation, the play feature may incorporate a timed playback aspect as described herein. An electrical power source 154 (shown in dotted lines), such as a battery or the like, may be provided in the storage unit 140 to power the record and playback features as well as any powered element in the toothbrush 120. For example, a vibration generator 122 (shown in dotted lines) may be located in the neck 123 to generate vibrations in the head 124. The generator 122 can be powered by the power source 154.

Alternatively, the storage unit 140 may plug into an outlet using a supplied cable connection (not shown). Other control configurations may be used. In accordance with at least one aspect of the present disclosure, the storage unit 140 of toothbrush 120 may be configured so that the functions associated with the record button 150 and the play button 152 may be operational as a single button. In such a configuration, storage unit 140 may determine whether the input 144 is connected to a signal source 160, in order to receive audio signal(s) when the single button is activated, or whether the input 144 is connected to toothbrush 120, in order to play the audio signal (s) when the single button is activated. Although shown as a push button type input, button 128, record button 150, and/or play button 152 may be any of a number of other types of input mechanisms or devices.

In accordance with at least one aspect of the present disclosure, a user may connect toothbrush 120 to a signal source 160 (here shown as an APPLE® IPOD® for example) and activate the signal transfer from the source 160 to the memory 146 using a play button on the signal source (not shown) and the record button 150. The record button 150 may be depressed once to record a certain period of music, such as three minutes for example, or it may be held down for a period of time equal to the amount of music transferred.

The user then activates a timed playback of the stored music through the speaker 148 by pressing play button 152 to play music for, for example, two minutes upon pressing and holding button 152 for two seconds, or three minutes upon pressing and holding button 152 for three seconds. Other durations may be set, which can correlate with a time period other than two or three minutes, or it can designate a specific number of songs. Alternatively, toothbrush 120 may be configured so that a user may simply press the play button 152 if a timed playback is not desired. Nevertheless, while any type of musical or non-musical audio signals may be stored in the memory, the toothbrush 120 advantageously enables the user to play audio signals pleasurable to him or her. In this way, the user can have an enjoyable brushing experience and will likely brush his or her teeth for the entire playback duration.

Any audio content may be used. In various scenarios of use, for children and teens, the audio signals may comprise audio digital webcasts, musical segments from a radio, satellite audio device, computer network (e.g., Internet), or the user's audio collection and the like. In one scenario, for adults, the audio signals may comprise information-based news summaries or stock reports for example that are automatically downloaded from the Internet. These various functions of the toothbrush enhance the brushing experience and enables longer duration brushing for improved oral hygiene. Any type of signal, such as audio and/or video, can be stored in the digital memory 146 of the toothbrush assembly 100, as long as the toothbrush assembly 100 includes an appropriate output to present such signal to a user. In one aspect, toothbrush assembly 100 also may include a display screen (not shown) to display video signals stored in the storage unit 140. Such uses, provide for musical videos to be played on the toothbrush 100, for example.

Any number of types of external audio and/or video sources may be utilized including an MP3 player, a CD player, a cassette player, a computer, a satellite audio/video receiver, or handheld digital satellite audio device and/or other signal sources.

In the aspects of the oral device described to follow, the operation of recording and/or storing audio signals, such as music, in a storage unit, for future playback is in accordance with the embodiments of FIGS. 1-4. Furthermore, the described signal source may be any external source as long as the signals are capable of being communicated and transferred from the source to the toothbrush assembly. Thus, the connection between the storage unit and the signal source does not have to be a direct physical connection, but could be a wireless connection that utilizes, for example, Bluetooth® technology or the like. The various illustrative arrangements of toothbrushes described herein each creates an environment that makes tooth brushing enjoyable and more likely to be maintained for at least the dentist-recommended period of time.

In one operation, the storage unit 140 is removed from the body 125 (FIG. 3) and connected to a signal source 160 by a direct connection with the input 144. In the embodiments of FIGS. 1-4 the input 144 generally comprises a headphone jack that extends outwardly from the storage unit 140. The input 144 is concealed within the body 125 of the toothbrush 120 when the storage unit 140 is connected thereto. Nevertheless, other input connections are contemplated, such as a Universal Serial Bus (USB) connector/adapter, which may be covered during use of the toothbrush 100 by a protecting cap (not shown), and which may function to both communicate with a signal source 160 and a power source 154 such as a recharging base (not shown). In this regard, the physical attachment of the input 144 with the body 125 does not result in signals being transferred from the storage unit 140 to the body 125. The outward extension of the input 144 allows the storage unit 140 to be directly connected or attached to the source 160 at a convenient location. The record button 150 and play button 152 function in a similar manner as described before, and a timed playback feature could be incorporated as described above.

Button 128 may be configured to operate as a single input button for multiple modes of operation of the toothbrush 100. Button 128 may be configured to operate in a number of different manners based upon how long the button 128 is depressed, how many times the button 128 is depressed, and/or the area of button 128 that is depressed. Single mode of operation button 128 may be configured to operate motorized elements of toothbrush 100 and output music and/or other audio in accordance with one or more modes of operation.

In accordance with one mode, the toothbrush 100 may be motorized for movement of one or more cleaning elements and music and/or other audio may be outputted from a speaker at a high volume. In accordance with another mode, the toothbrush 100 may be motorized for movement of one or more cleaning elements and music and/or other audio may be outputted from a speaker at a low volume. In accordance with still another mode, the toothbrush 100 may be motorized for movement of one or more cleaning elements and no music and/or other audio may be outputted from a speaker. In accordance with yet another mode, the toothbrush 100 may not be motorized for movement of one or more cleaning elements and music and/or other audio may be outputted from a speaker.

Any of a number of different operations of the motorized cleaning elements of the toothbrush 100 and/or the music or other audio output may be configured for a mode of operation in accordance with one or more aspects of the present disclosure described herein. For example, one mode of operation may be to output music or other audio from a particular file, such as a particular play list of the user that is stored in the toothbrush 100. In another mode of operation, the speed of the motorized cleaning elements of the toothbrush 100 may change in accordance with music tempo, volume, or other features. Any of a number of different modes of operation of the moving elements of toothbrush 100 and/or the music or other audio output from toothbrush 100 may be utilized in accordance with one or more aspects of the present disclosure.

Figure 10:
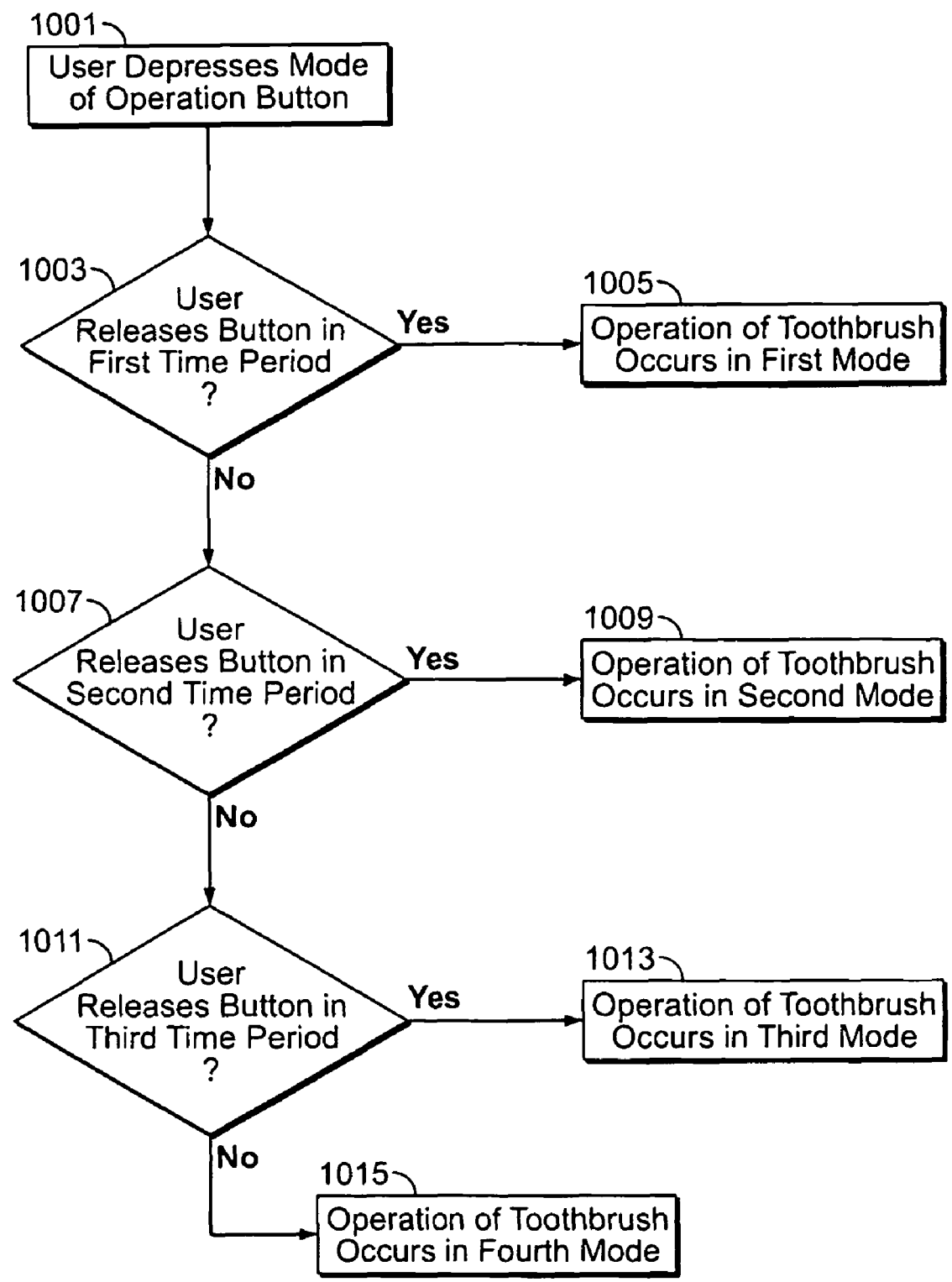
FIG. 10 is a flow chart of an illustrative method for changing a mode of operation of a toothbrush described herein.
Figure 11:
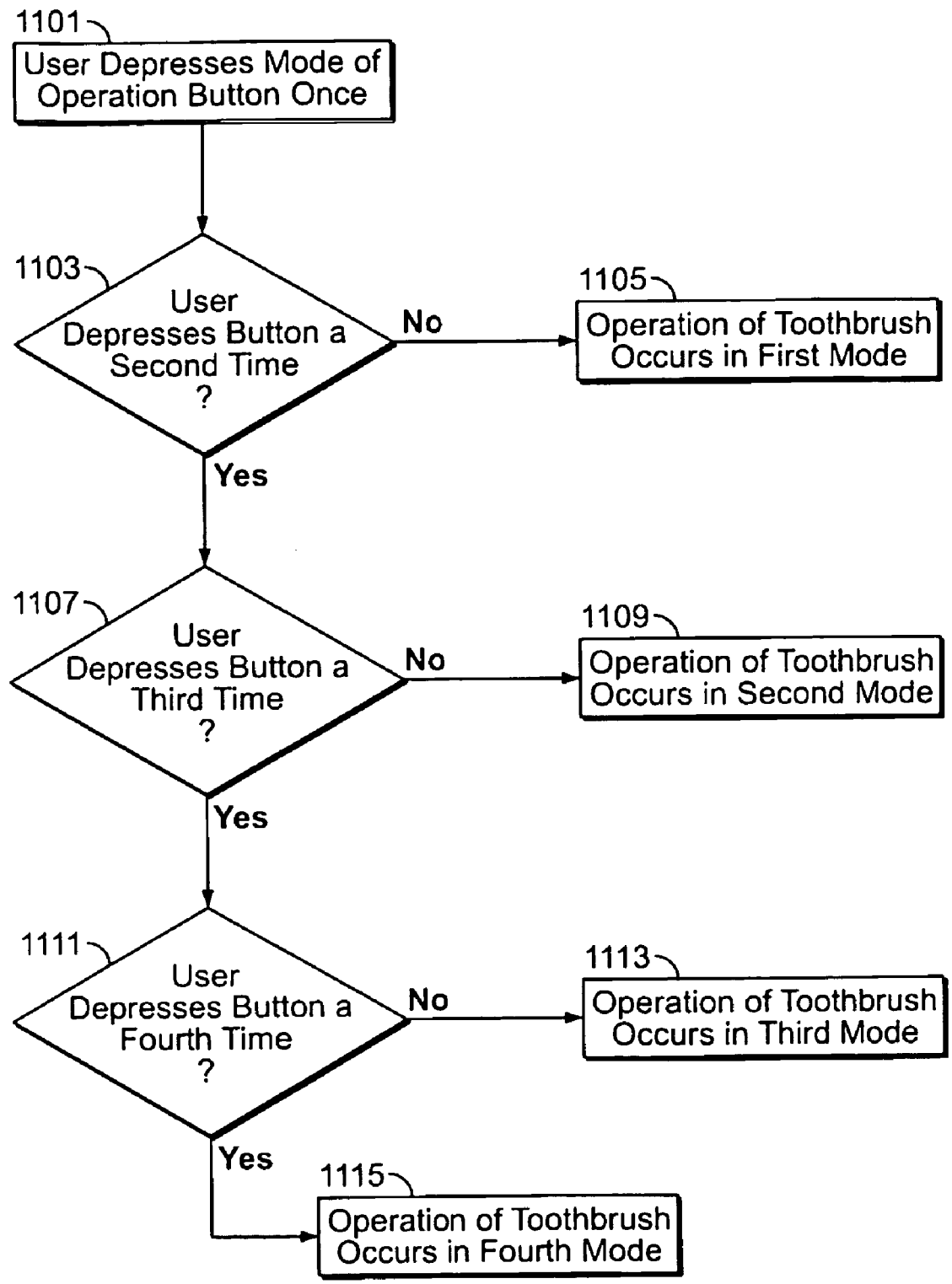
FIG. 11 is a flow chart of another illustrative method for changing a mode of operation of a toothbrush described herein.
Figure 12:
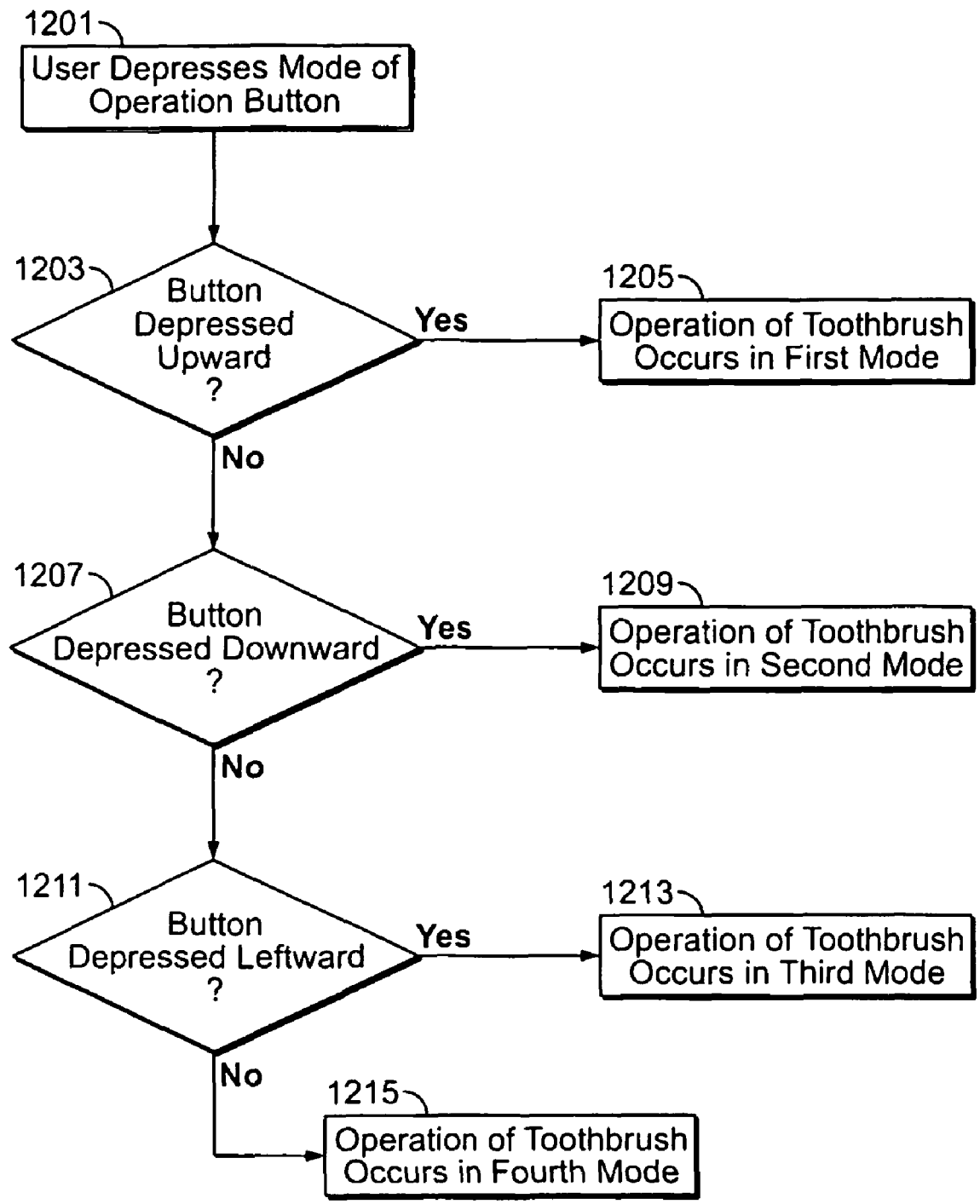
FIG. 12 is a flow chart of another illustrative method for changing a mode of operation of a toothbrush described herein.

FIGS. 10-12 illustrate methods for changing a mode of operation of a toothbrush in accordance with at least one aspect of the present disclosure. A mode of operation may be changed using a number of different input schemes. FIG. 10 illustrates an example where the mode of operation of a toothbrush is configured to change based upon how long a user of the toothbrush depresses a mode of operation button on the toothbrush before releasing the depression. Different modes of operation may use different volumes for audio output, use different vibrations for one or more powered cleaning elements of the toothbrush, power the audio output and not power the powered cleaning elements, power the cleaning elements and not power the audio output, use different audio signals for output from the audio output, etc.

The process begins and at step 1001, a user of a toothbrush in accordance with one or more features of the present disclosure depresses a mode of operation button on the toothbrush. For example, with respect to FIG. 1, the user may depress mode of operation button 128. The method then moves to step 1003.

In step 1003, a determination is made as to whether the user has released the depressed mode of operation button within a first time period. For example, a first time period may be defined to be one second. If a user depresses the mode of operation button and releases the button after two seconds, the determination of step 1003 would be that the user did not release the depressed mode of operation button within the first time period, i.e., within one second. If the user did release the mode of operation button within the first time period, the process moves to step 1005 where the operation of the toothbrush occurs in a first mode of operation. Such a condition may be that the toothbrush is motorized to operate and music and/or other audio is outputted from the toothbrush at a high volume. If the user did not release the mode of operation button within the first time period in step 1003, the process moves to step 1007.

In step 1007, a determination is made as to whether the user has released the depressed mode of operation button within a second time period. For example, a second time period may be defined to be more than one second up to and including two seconds. If a user depresses the mode of operation button and releases the button after three seconds, the determination of step 1007 would be that the user did not release the depressed mode of operation button within the second time period, i.e., between more than one second and two seconds. If the user did release the mode of operation button within the second time period, the process moves to step 1009 where the operation of the toothbrush occurs in a second mode of operation. Such a condition may be that the toothbrush is motorized to operate and music and/or other audio is outputted from the toothbrush at a low volume. If the user did not release the mode of operation button within the second time period in step 1009, the process moves to step 1011.

In step 1011, a determination is made as to whether the user has released the depressed mode of operation button within a third time period. For example, a third time period may be defined to be more than two seconds up to and including three seconds. If a user depresses the mode of operation button and releases the button after four seconds, the determination of step 1011 would be that the user did not release the depressed mode of operation button within the third time period, i.e., between more than two seconds and three seconds. If the user did release the mode of operation button within the third time period, the process moves to step 1013 where the operation of the toothbrush occurs in a third mode of operation. Such a condition may be that the toothbrush is motorized to operate and music and/or other audio is not outputted from the toothbrush. If the user did not release the mode of operation button within the third time period in step 1011, the process moves to step 1015, where the operation of the toothbrush occurs in a fourth mode of operation. Such a condition may be that the toothbrush is not motorized to operate and music and/or other audio is outputted from the toothbrush.

FIG. 11 illustrates an example where the mode of operation of a toothbrush is configured to change based upon how many times a user of the toothbrush depresses a mode of operation button on the toothbrush. The process begins and at step 1101, a user of a toothbrush in accordance with one or more features of the present disclosure depresses a mode of operation button on the toothbrush a single time. For example, with respect to FIG. 1, the user may depress mode of operation button 128. The method then moves to step 1103.

In step 1103, a determination is made as to whether the user has depressed the mode of operation button a second time within a specified time period before locking on a particular mode of operation. For example, a specified time period may be defined to lock to a particular mode of operation if no depression of the mode of operation button occurs after two seconds from the previous depression. If a user depresses the mode of operation button in step 1101 and then does not depress the mode of operation button again within the specified time period in step 1103, the determination of step 1103 would move to step 1105 to indicate that the user did not depress the mode of operation button a second time and the operation of the toothbrush occurs within a first mode of operation. Such a condition may be that the toothbrush is motorized to operate and music and/or other audio is outputted from the toothbrush at a high volume. If the user did depress the mode of operation button a second time in step 1103, the process moves to step 1107.

In step 1107, a determination is made as to whether the user has depressed the mode of operation button a third time within a specified time period before locking on a particular mode of operation. For example, a specified time period may be defined to lock to a particular mode of operation if no depression of the mode of operation button occurs after two seconds from the previous depression. If a user does not depress the mode of operation button again within the specified time period in step 1107, the determination of step 1107 would move to step 1109 to indicate that the user did not depress the mode of operation button a third time and the operation of the toothbrush occurs within a second mode of operation. Such a condition may be that the toothbrush is motorized to operate and music and/or other audio is outputted from the toothbrush at a low volume. If the user did depress the mode of operation button a third time in step 1107, the process moves to step 1111.

In step 1111, a determination is made as to whether the user has depressed the mode of operation button a fourth time within a specified time period before locking on a particular mode of operation. For example, a specified time period may be defined to lock to a particular mode of operation if no depression of the mode of operation button occurs after two seconds from the previous depression. If a user does not depress the mode of operation button again within the specified time period in step 1111, the determination of step 1111 would move to step 1113 to indicate that the user did not depress the mode of operation button a fourth time and the operation of the toothbrush occurs within a third mode of operation. Such a condition may be that the toothbrush is motorized to operate and music and/or other audio is not outputted from the toothbrush. If the user did depress the mode of operation button a fourth time in step 1111, the process moves to step 1115, to indicate operation of the toothbrush to occur within a fourth mode of operation. Such a condition may be that the toothbrush is not motorized to operate and music and/or other audio is outputted from the toothbrush.

FIG. 12 illustrates an example where the mode of operation of a toothbrush is configured to change based upon how a user of the toothbrush depresses a mode of operation button on the toothbrush. The process begins and at step 1201, a user of a toothbrush in accordance with one or more features of the present disclosure depresses a mode of operation button on the toothbrush a single time. For example, with respect to FIG. 1, the user may depress mode of operation button 128. The method then moves to step 1203.

Figure 13A:
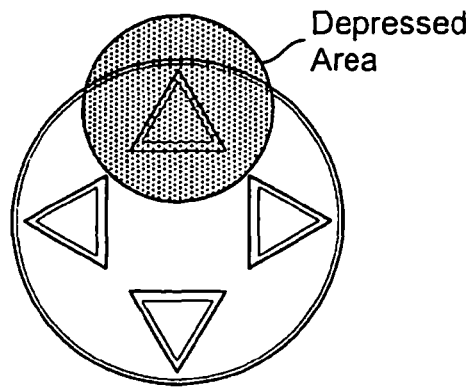
FIGS. 13A-13C are top views of an example of depression of a mode of operation button for a toothbrush described herein.

In step 1203, a determination is made as to whether the user has depressed the mode of operation button in an upward direction, e.g., with more force applied to the top of the button as shown in FIG. 13A. If a user depresses the mode of operation button in step 1201, and in an upward direction, the determination of step 1203 would move to step 1205 to operate of the toothbrush within a first mode of operation. Such a condition may be that the toothbrush is motorized to operate and music and/or other audio is outputted from the toothbrush at a high volume. If the user did not depress the mode of operation button in an upward direction in step 1203, the process moves to step 1207.

Figure 13B:
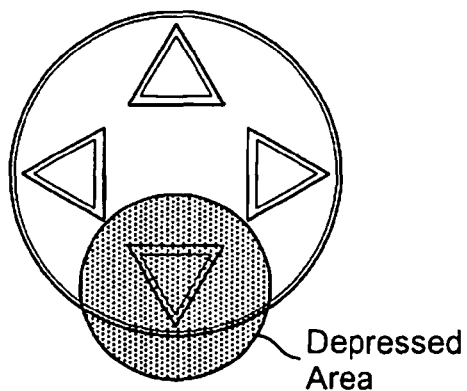

In step 1207, a determination is made as to whether the user has depressed the mode of operation button in a downward direction, e.g., with more force applied to the bottom of the button as shown in FIG. 13B. If a user depresses the mode of operation button in a downward direction, the determination of step 1207 would move to step 1209 to operate the toothbrush within a second mode of operation. Such a condition may be that the toothbrush is motorized to operate and music and/or other audio is outputted from the toothbrush at a low volume. If the user did not depress the mode of operation button in a downward direction in step 1207, the process moves to step 1211.

Figure 13C:
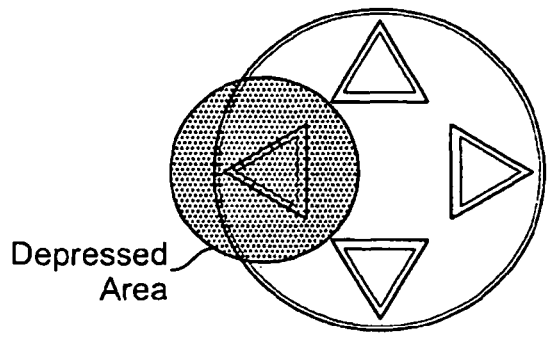

In step 1211, a determination is made as to whether the user has depressed the mode of operation button in a leftward direction, e.g., with more force applied to the left side of the button as shown in FIG. 13C. If a user depresses the mode of operation button in a leftward direction, the determination of step 1211 would move to step 1213 to operate the toothbrush within a third mode of operation. Such a condition may be that the toothbrush is motorized to operate and music and/or other audio is not outputted from the toothbrush. If the user did not depress the mode of operation button in a leftward direction in step 1211, the process moves to step 1215 to operate the toothbrush within a fourth mode of operation. Such a condition may be that the toothbrush is not motorized to operate and music and/or other audio is outputted from the toothbrush.

Any of a number of different modes of operation of the toothbrush at certain speeds and/or music or other audio output at certain volumes may be utilized in accordance with one or more aspects of the present disclosure described herein and the present disclosure is not limited to the illustrative examples provided.

Figure 5:
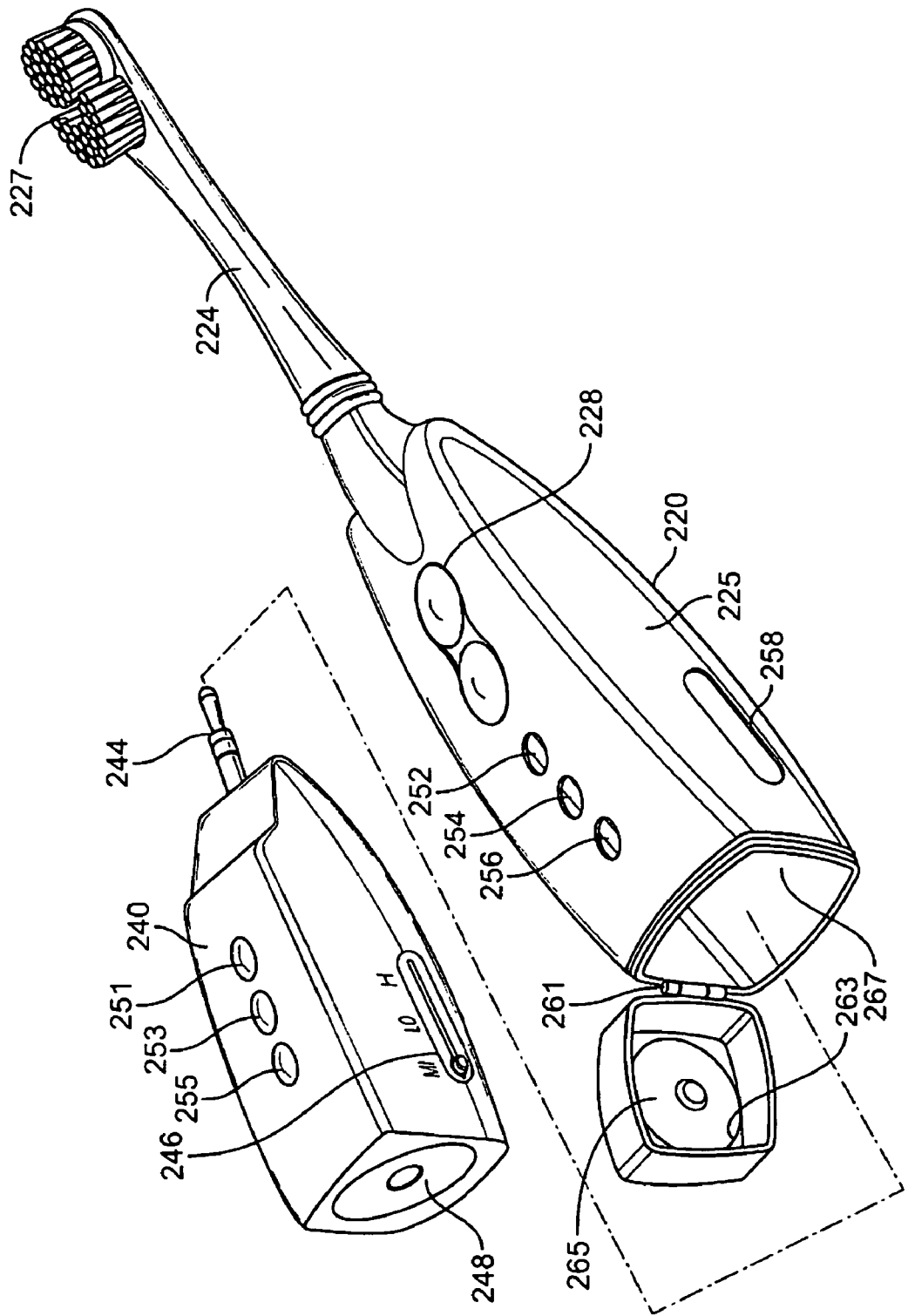
FIG. 5 is an exploded view of an example of a toothbrush described herein.

FIGS. 5-6 illustrate another toothbrush assembly in accordance with at least one aspect of the present disclosure. The toothbrush assembly may include a power toothbrush 220 having a body 225, a removable storage unit 240 that may be inserted into an opening or cavity 267 of body 225, and a button 228. The toothbrush 220 further may include a head 224 having cleaning elements 227. The cleaning elements 227 further comprise any known cleaning elements used in toothbrushes or other oral care implements, such as, but not limited to nylon bristles, tufts of bristles, bristle walls, elastomeric elements, and the like. The toothbrush 220 may be a power toothbrush including a motor/power source 271 (e.g., motor and battery combination, for example) that drives a shaft or rotor 273 for a powered element, such as movable cleaning elements 227. Toothbrush 220, as shown, also may include a latching door 263 that is operatively connected to the body 225 by a latching mechanism 261. Door 263, as shown, may include a grill 265 to allow for output of audio from a speaker. Any of a number of different types and/or configurations of door 267 and/or latching mechanism 261 may be utilized. For example, door 263 may be a threaded type so as to matingly engage the bottom of body 225 for closing the cavity 267. Nevertheless, other configurations are possible.

The removable storage unit 240 is similar in many respects to the removable storage unit 120. Storage unit 240 is configured to be housed within cavity 267 of the body 225 of toothbrush 220. In an alternative configuration described above, removable storage unit 140 is configured to be a portion of the outside surface of handle 126 or a portion of handle 126.

The removable storage unit 240 further comprises an input 244 for connection to a source device (not shown), a memory (not shown) for storing audio and/or video signal(s) received via the input 244, and an output 248 in the form of an integrated speaker positioned on the underside of the unit 240 for transmitting the stored signal(s) through grill 265 to the user's surroundings when the storage unit 240 is positioned within the body 225 of toothbrush 220. Input 244 may be a standard headphone jack. Storage unit 240 further may include a volume control 246 to allow a user to set the level of output through the speaker 248. The volume control 246 can be a slide switch, dial and the like. When housed within the opening 263 of the body 225 of toothbrush 220, volume control 246 may be configured to be depressible or slidable through aperture control 258. The aperture control 258 may have a thin elastomeric material covering so that volume control 246 may be operated while maintaining a liquid seal of the cavity 267. In one exemplary arrangement, storage unit 240 may includes a record button for recording the audio and/or video signal(s) to the memory. In the arrangement, the storage unit 240 may be configured to automatically record when sound from the source device (not shown) is detected. The sound from a source device triggers the storage unit 240 to record audio signals.

Storage unit 240 may include one or more a play buttons 251, 253, and 255 for playing recorded audio and/or video signal(s). For example, the storage unit 240 may store three separate songs. When housed within the opening 263 of the body 225 of toothbrush 220, button 251, 253, and 255 may be configured to be depressible through aperture 252, 254, and 256, respectively. The aperture 252, 254, 256 may have a thin elastomeric material covering so that buttons 251, 253, and 255 may be depressible through body 225, while maintaining a liquid seal of the cavity 267.

Upon activation/interaction with button 251, a first audio file may be outputted to the speaker 248. Alternatively, if button 255 is depressed, a third audio file may be outputted to the speaker 248. The use of different audio files may allow different people to use the same storage unit 240 in different personal toothbrushes 240 and/or may allow a single user to store multiple songs for playback purposes. In one such example, a parent may want a child to hear an upbeat song when brushing in the morning to motivate the child to start her day, while the parent may want the child to hear a bedtime song when brushing before bedtime to motivate the child to get ready to sleep.

The play feature may incorporate a timed playback feature as described above. A power source (e.g., battery) may be provided in the storage unit 240 to power the record and playback features as well as any powered element in the toothbrush 220. For example, a vibration generator may be located in the neck of toothbrush 220 to generate vibrations in the head 224, which generator is powered by the power source.

Alternatively, storage unit 240 may plug into an outlet using a supplied cable connection (not shown). Although shown as a push button type input, button 228, and play buttons 251, 253, and 255 may be any of a number of other types of input mechanisms.

As shown in FIG. 7, body 225 of toothbrush 220 may include an input socket 275. Input socket 275 may be configured to connect the power source 271 to the input 244. Input socket 275 may be a standard headphone plug input receiver. Input socket 275 may be configured internal to or external from the motor/power source 271. In the example shown in FIG. 7, input socket 275 is physically connected to motor/power source 271. In one arrangement, motor/power source 271 is attached to a connection determination unit 281. Connection determination unit 281 is configured to determine whether an input 244 is connected to the input socket 275. If an input 244 is detected by connection determination unit 281, toothbrush 220 is then configured to be able to play back audio and/or video signal(s) from storage unit 240 upon depression of a button, such as button 228.

Figure 8:
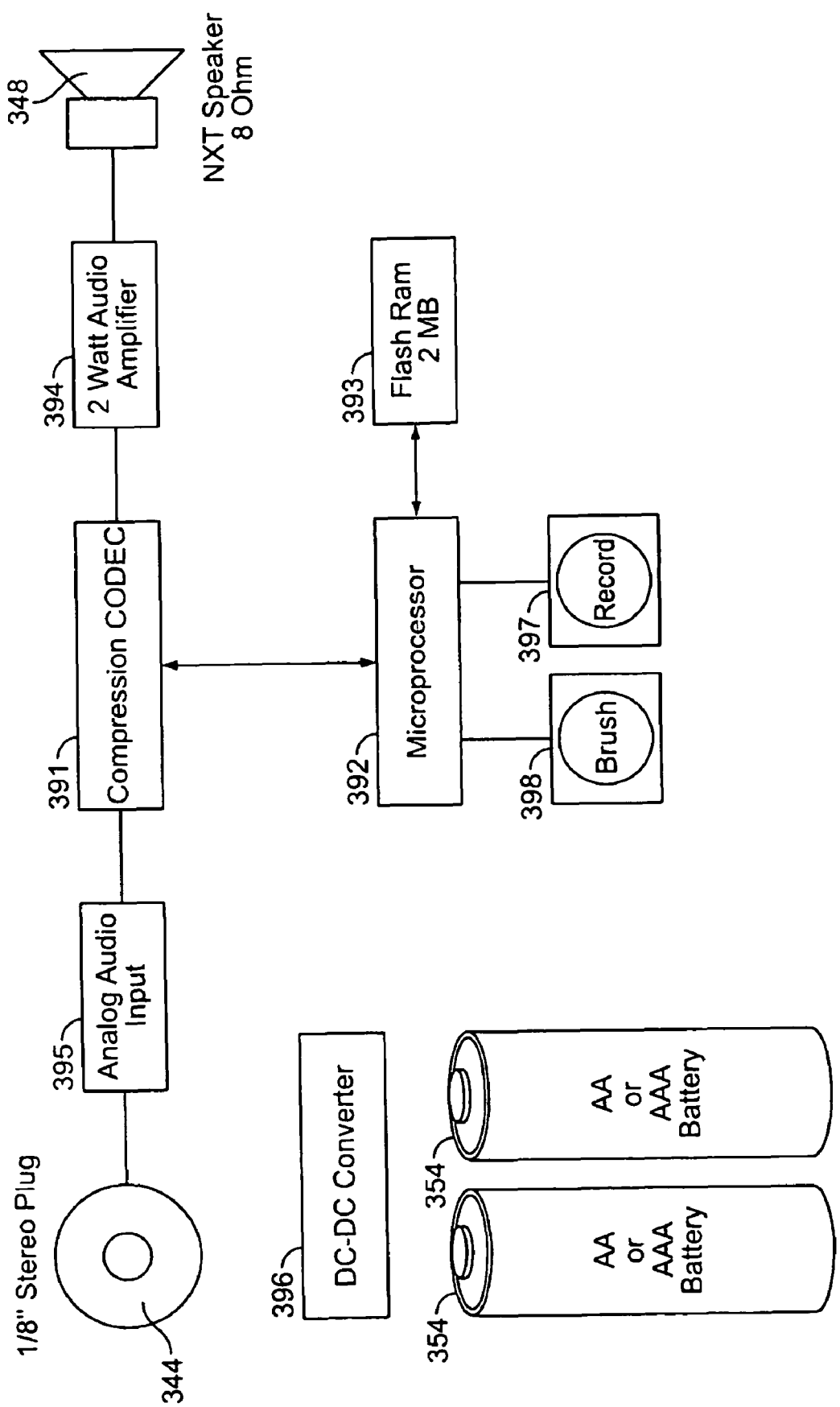
FIG. 8 is an example functional block diagram of components of a storage unit described herein.

FIG. 8 illustrates an exemplary block diagram of components of a storage unit in accordance with at least one aspect of the present disclosure. One or more of the components of FIG. 8 may be included within one or more printed circuit boards. An illustrative printed circuit board may be 18 mm×50 mm with a 16 kHz sample rate. As shown, the components of a storage unit may include an input plug 344 in the form of a ⅛ inch stereo plug coupled to an analog audio input component 395. An integrated speaker 348, such as an 8 Ohm NXT speaker, may be coupled to an amplifier 294, such as a 2 Watt audio amplifier. Input received from the input plug 344 through the analog audio input component 395 is sent to a compression CODEC 391. Signal(s) for output are sent to the speaker 348 though the amplifier 394 from the compression CODEC 391. Compression CODEC 391 is shown in communication with a microprocessor 392.

Microprocessor 392 is configured to perform all of the functions for processing signal(s), performing computer-readable instructions, and reading from and writing to a memory 393. As shown, microprocessor 392 communicates with a memory 393, such as a 2 MB flash RAM. Audio signals received via input plug 344 are stored in memory 393 and may be outputted to speaker 348. Power is provided by one or more batteries 354 to supply electrical power through a DC to DC converter 396 to one or more components of the storage unit.

Recordation component 397 is shown coupled to microprocessor 392. Recordation component 397 may include instructions for the microprocessor 392 to record the audio signal(s) to memory 393 through input plug 344. Brush component 398 is shown coupled to microprocessor 392. Brush component 398 may include instructions for the microprocessor 392 to operate a motor (not shown) for a powered element (not shown) such as movable cleaning elements. Instructions with respect to recordation component 397 and/or brush component 398 may be included within memory 393 and/or some other memory, such as a ROM memory.

In one aspect, an oral care device, such as a toothbrush, a tongue cleaner, and/or a flossing device, may be configured to automatically record sound when the sound from a source device is detected. The sound from a source device triggers the oral care device to record the audio signal, i.e., the sound.

In one aspect, an oral care device may include an oral care region attached to a body with a portion of the body being configured for gripping by a user as described herein. This oral care device further may include a memory within the body of the device. The memory may be configured to store one or more audio signals.

A processor, which may be located within the body of the oral care device, may be configured to automatically record to the memory an audio signal from an external audio source, such as an MP3 player, a CD player, a radio, a television, and a person's voice. The processor may be configured to automatically record when the audio signal is detected. As such, the detection of the audio signal triggers the recording of the signal without any user selection to actually record the audio signal. Finally, a speaker may be included in the oral care device to output the stored audio signal. Any of a number of components described herein may be included in such an oral care device as well. Such components may include, but are not limited to a play button on the body configured to activate the processor to send the stored audio signal to the speaker, the oral care region including tooth cleaning elements, a power source within the body, the oral care region including at least one powered element, and various operational buttons to activate/deactivate powered elements and/or the output of stored audio signals.

Figure 9:
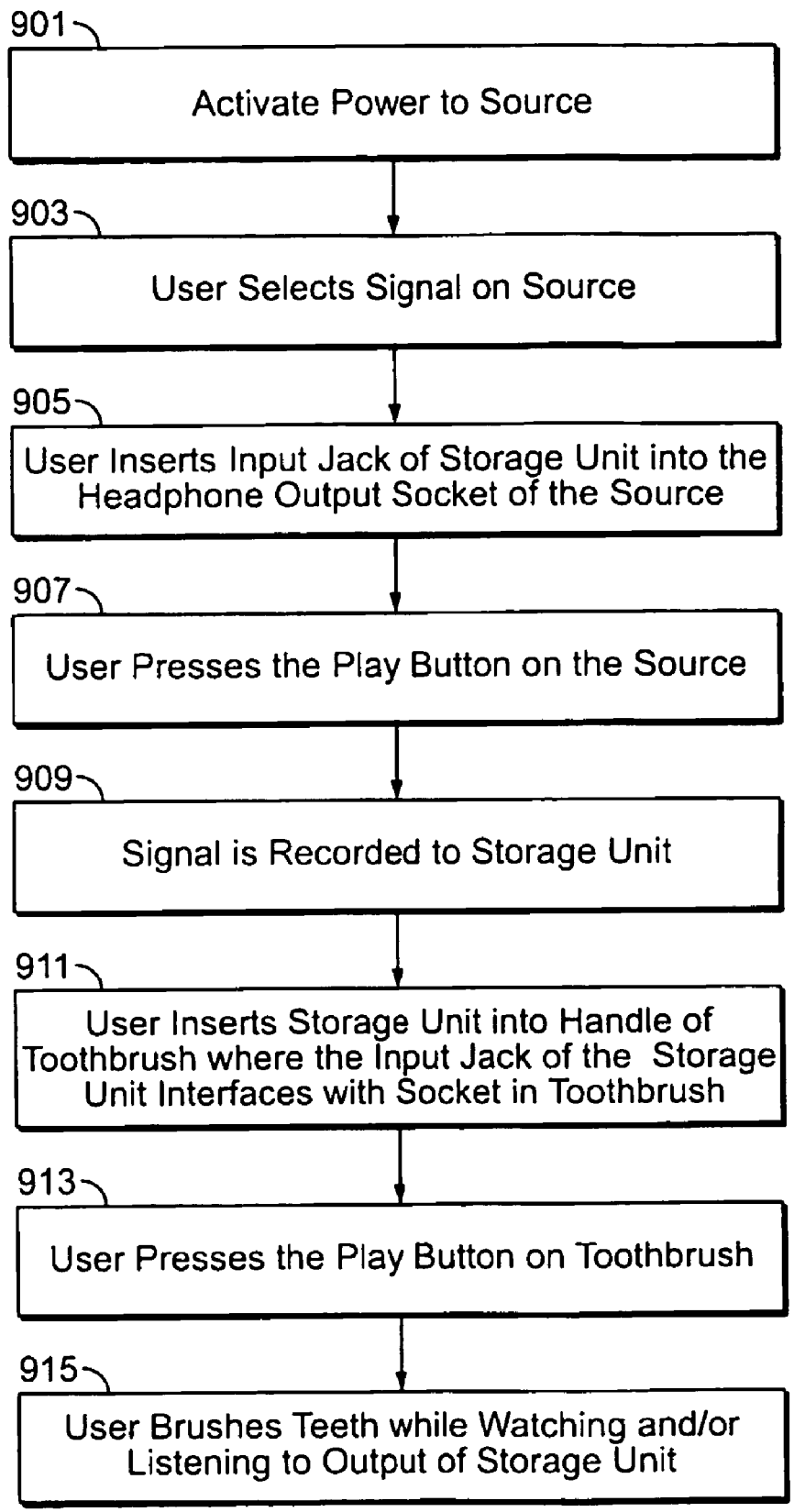
FIG. 9 is a flow chart of an illustrative method for transferring music or audio from a signal source to a toothbrush described herein.

FIG. 9 is a flow chart of an illustrative method for transferring music from a signal source to a toothbrush assembly in accordance with at least one aspect of the present disclosure. The process starts at step 901 where power to an external source, such as a music player, is activated by a user. Such may be the case when a user turns on the music player. At step 903, the user selects a particular signal on the source of interest. In one example, this may be a case where the user selects a particular 2-4 minutes song to be recorded. Proceeding to step 905, the user inserts the input headphone jack of a storage unit, such as input 244 of storage unit 240, into the headphone output socket of the source device, such as source device 160. At this point, although not shown, the user may set the output level of the source device to medium or low.

At step 907, the user presses the play button on the source device to play the selected song of interest. The storage unit may be configured to trigger recordation of the song when sound is detected. Alternatively, a record button, such as record button 150, associated with the storage unit may be depressed by the user to start the recordation process. In any configuration, at step 909, the selected signal of interest is recorded in the memory of the storage unit, such as memory 393. While the storage unit is recording, a previous file or song can be automatically overwritten. Upon completion of the recordation of the song and proceeding to step 911, the user inserts the storage unit into the handle of a toothbrush where the input jack of the storage unit interfaces with a socket in the toothbrush. Such an illustrative configuration is shown in FIG. 7 where input socket 275 of toothbrush 220 interfaces with input 244 of storage unit 240. In this example, storage unit 244 is shown in the body 225 of toothbrush 220.

At step 913, the user presses the play button on the toothbrush. In one such example shown in FIG. 6, the user may depress button 228 to activate the output of music. Finally, at step 915, the user brushes her teeth with the toothbrush while watching and/or listening to output from the storage unit. For example, if a song of interest has been recorded, the song is outputted through a speaker, such as speaker 248. In one configuration, the time for the song may correlate to the desired amount of time for the user to brush her teeth, such as two minutes.

Referring to FIGS. 1 and 5, in another aspect, a vibratory device 122 can be provided to vibrate the toothbrush 120, 220 or a portion thereof, such as the head 124, 224 or a portion thereof. The vibration-producing device can be used to vibrate tooth cleaning elements 127, 227 and/or soft tissue cleaning elements.

A wide variety of vibratory devices can be used to produce vibrations over a wide range of frequencies to meet the needs of a particular application. Various types of vibratory devices are commercially available, such as transducers. One example of a vibratory device provides frequencies in the range of about 100 to 350 kHz. The vibration frequencies may be of different waveforms, including sinusoid, square, sawtooth and the like. Nevertheless, other values and waveforms are possible. A vibratory device may be located in head of the toothbrush or neck thereof. When activated, the vibratory device is powered by battery (and controlled by electronics on the circuit board or switching system) so as to induce vibrations in the head of the toothbrush and thereby enhance teeth-cleaning action imparted by the tooth cleaning elements. In alternate embodiments, a vibratory device may include a micro motor attached to a shaft, with the shaft coupled to an eccentric rotating about an axis parallel to the longitudinal axis of the toothbrush. In still other embodiments, a vibratory-producing device may include an eccentric that is driven by a micro motor in a translatory manner.

A switch, such as a button 128, 228, toggle switch, rotating dial, or the like, can be provided for activating the vibratory device. A vibratory device often has a power source, such as a battery. Activating the switch can cause the vibration-producing device to operate for a user-defined interval (e.g., during the time that a button is depressed or a switch is in an engaged position), or alternatively can activate a timing circuit that causes the vibratory device to operate for a predetermined interval. If a timing circuit is used, the associated interval either may be preset or may be adjustable, e.g., by a user-activated rotating dial.

Additional operational configurations may exist in order to control one or more aspects of a motor utilized in accordance with one or more aspects of the present disclosure. Controls configurations in the form of circuitry, software, and/or firmware may be utilized in accordance with one or more aspects of the present disclosure in order to control aspects of a motor for moving cleaning elements or other components of a toothbrush in accordance with one or more aspects of the present disclosure. Controls may be implemented to maintain a constant voltage on the motor. In such a condition, the voltage across the motor may remain generally the same during operation regardless of the load placed on the motor, such as by the force applied by a user brushing her teeth. The voltage may be monitored to ensure a particular level is maintained. Other controls may be implemented to maintain a constant speed of operation of the motor. In such a condition, the speed of operation of the motor may be monitored and the voltage applied to the motor may be adjusted periodically to compensate for load fluctuations and maintain a constant speed regardless of the load.

In one embodiment, referring to FIGS. 1, 3, 5 and 6, a ratio of the length of the neck 123, 223 and head 124, 224 to the height of the toothbrush (measured from the distal bottom end 149 to the distal top of head 124, 224) ranges from 1:10 to 2:5. In another example, the noted neck/head length to the toothbrush height ratio ranges from 1:20 to 1:30. Nevertheless, other values of the noted ratios are possible. In one embodiment, the external height of the toothbrush, ergonomically sized for children, ranges from about 160 mm to 200 mm. In other arrangements, the height of the toothbrush ranges from about 160 mm to 194 mm; to less than 194 mm or 190 mm. Nevertheless, other heights of the toothbrush assembles are possible. In one arrangement, the width of the handle 10 can range between 19 mm to 28 mm. In another arrangement, the depth of the handle 10 ranges between 19 mm to 27 mm. In other embodiments, the depth ranges between 19 mm to 21 mm. In a cylindrical configuration, the handle 10 may have a diameter ranging from 19 mm to 28 mm. Nevertheless, other values are possible. These ergonomic configurations provide for a toothbrush to have a neck/head length to reach within the depth of the oral cavity, while balancing the need for musculoskeletal strength of a child to manipulate the toothbrush. Accordingly, these configurations or combinations thereof enable an easily maneuverable electric toothbrush for children and provide for an enjoyable brushing experience to improve oral hygiene.

Designations such as "first" and "second" are for illustrative purposes and can be interchanged. While the disclosure has been described with respect to specific examples including presently preferred modes of carrying out the disclosure, those skilled in the art will appreciate that there are numerous variations and permutations of the above described systems and techniques. Thus, the spirit and scope of the disclosure should be construed broadly as set forth in the appended claims.

The invention claimed is:

1. A toothbrush, comprising:
a body with a speaker, the bottom of the body configured to rest against a support surface when the toothbrush is oriented in a standing position; and
the speaker configured to output an audio signal through an opening on the body of the toothbrush, the speaker and the opening are angled at an acute angle relative to the support surface and with respect to the bottom of the body to prevent water from contacting the speaker when the toothbrush is in the standing position.

2. The toothbrush of claim 1, comprising wherein the speaker is located adjacent to the bottom of the body.

3. A toothbrush, comprising:
a body configured to store an audio component, the audio component configured to be removably housed within a cavity of the body; and
the audio component configured to operate as a microphone to receive an audio signal in a first mode of operation and to operate as a speaker to output the audio signal through the body of the toothbrush in a second mode of operation.

4. The toothbrush of claim 3, further comprising:
a memory configured to store the audio signal, the memory being located within the body of the toothbrush.

5. The toothbrush of claim 3, further comprising an operation mode button configured to activate a processor to change operation of the audio component between the first mode of operation and the second mode of operation.

6. A toothbrush, comprising:
a storage unit including an output for transmitting a stored audio signal and a power source, wherein the storage unit is configured to be removably housed within a cavity of a body;
an oral care region attached to the body, a portion of the body being configured for gripping by a user, the oral care region including tooth cleaning elements configured to move when powered by the power source; and
a single operation mode button configured to change a mode of operation of the toothbrush,
wherein in a first mode of operation, the tooth cleaning elements are powered by the power supply and the stored audio signal is transmitted through the output,
wherein in a second mode of operation, the tooth cleaning elements are not powered and the stored audio signal is transmitted through the output.

7. The toothbrush of claim 6, wherein the single operation mode button is configured to change the mode of operation of the toothbrush based upon how long the single operation mode button is depressed.

8. The toothbrush of claim 6, wherein the single operation mode button is configured to change the mode of operation of the toothbrush based upon how many times the single operation mode button is depressed.

9. The toothbrush of claim 6, the single operation mode button including a plurality of depressible locations, wherein the single operation mode button is configured to change the mode of operation of the toothbrush based upon a location of depression on the single operation mode button of the plurality of depressible locations.

10. The toothbrush of claim 9, wherein depression of the single operation mode button at a first location of the plurality of depressible locations operates the toothbrush in the first mode of operation, and depression of the single operation mode button at a second location of the plurality of depressible locations operates the toothbrush in the second mode of operation, the first and second locations being different.

11. The toothbrush of claim 6, wherein in a third mode of operation, the tooth cleaning elements are powered by the power supply and the stored audio signal is not transmitted through the output.

* * * * *